United States Patent [19]

DesMarais et al.

[11] Patent Number: 5,250,576
[45] Date of Patent: Oct. 5, 1993

[54] PROCESS FOR PREPARING EMULSIONS THAT ARE POLYMERIZABLE TO ABSORBENT FOAM MATERIALS

[75] Inventors: Thomas A. DesMarais, Norwood; Stephen T. Dick, Blue Ash; Thomas M. Shiveley, Moscow, all of Ohio

[73] Assignee: The Procter & Gamble Company, Cincinnati, Ohio

[21] Appl. No.: 12,675

[22] Filed: Feb. 3, 1993

Related U.S. Application Data

[60] Division of Ser. No. 935,935, Aug. 27, 1992, Pat. No. 5,198,472, which is a division of Ser. No. 830,159, Feb. 3, 1992, Pat. No. 5,149,720, which is a continuation-in-part of Ser. No. 743,947, Aug. 12, 1991, abandoned.

[51] Int. Cl.$^5$ .............................. C08J 9/26; C08J 9/28
[52] U.S. Cl. .......................... 521/63; 521/61; 521/64; 521/146; 521/149; 521/150; 524/801; 524/804
[58] Field of Search ................. 521/61, 63, 64, 146, 521/149, 150; 524/801, 804

[56] References Cited

U.S. PATENT DOCUMENTS

| | | | |
|---|---|---|---|
| 3,255,127 | 6/1966 | von Bonin | 260/2.5 |
| 3,565,817 | 2/1971 | Lissant | 252/312 |
| 3,734,867 | 5/1973 | Will | 260/2.5 R |
| 3,763,056 | 10/1973 | Will | 260/2.5 L |
| 3,988,508 | 10/1976 | Lissant | 526/344 |
| 4,473,611 | 9/1984 | Haq | 428/198 |
| 4,522,953 | 6/1985 | Barby et al. | 521/64 |
| 4,606,958 | 8/1986 | Haq et al. | 428/68 |
| 4,612,334 | 9/1986 | Jones et al. | 521/146 |
| 4,659,564 | 4/1987 | Cox et al. | 424/65 |
| 4,668,709 | 5/1987 | Jones et al. | 521/146 |
| 4,788,225 | 11/1988 | Edwards et al. | 521/147 |
| 4,797,310 | 1/1989 | Barby et al. | 428/71 |
| 4,839,395 | 6/1989 | Masamizu et al. | 521/56 |
| 5,147,345 | 9/1992 | Young et al. | 604/378 |
| 5,149,720 | 9/1992 | DesMarais et al. | 521/63 |
| 5,198,472 | 3/1993 | DesMarais et al. | 521/63 |

FOREIGN PATENT DOCUMENTS 299762 1/1989 European Pat. Off. .
2194166A 3/1988 United Kingdom .

OTHER PUBLICATIONS

Lissant et al—"Structure of High-Internal-Phase-Ratio Emulsions," Journal of Colloid and Interface Science, vol. 47, No. 2, May 1974.
Lissant et al—"A Study of Medium and High Internal Phase Ratio Water/Polymer Emulsions," Journal of Colloid and Interface Science, vol. 42, No. 1, Jan. 1973.
Lissant—"The Geometry of High-Internal Phase-Ratio Emulsions," Journal of Colloid and Interface Science, vol. 22, 462–468 (1966).

*Primary Examiner*—Morton Foelak
*Attorney, Agent, or Firm*—Eric W. Guttag; E. Kelly Linman

[57] ABSTRACT

Disclosed is a process for the continuous preparation of high internal phase emulsions which are suitable for subsequent polymerization into polymeric foam materials that, upon dewatering, act as absorbents for aqueous body fluids. The process involves continuous introduction of a certain type of monomer-containing oil phase and a certain type of electrolyte-containing water phase into a dynamic mixing zone at relatively low water to oil phase ratios. Flow rates are then steadily adjusted to increase the water to oil ratio of the streams fed to the dynamic mixing zone while subjecting the dynamic mixing zone contents to shear agitation which is sufficient to thereby form a high internal phase emulsion that, upon subsequent polymerization, provides a foam having an average cell size of from about 5 to 100 microns. The formation of such a stable high internal phase emulsion is completed by feeding the contents of the dynamic mixing zone to and through a static mixing zone.

3 Claims, 2 Drawing Sheets

0 10u

PROCESS FOR PREPARING EMULSIONS THAT ARE POLYMERIZABLE TO ABSORBENT FOAM MATERIALS

CROSS-REFERENCE TO RELATED APPLICATION

This is a division of application Ser. No. 07/935,935, filed on Aug. 27, 1992, now U.S. Pat. No. 5,198,472 which is a division of application Ser. No. 07/830,159, filed on Feb. 3, 1992, now U.S. Pat. No. 5,149,720, which is a continuation-in-part of application Ser. No. 07/743,947, filed Aug. 12, 1991, now abandoned.

FIELD OF THE INVENTION

This invention relates to a continuous process for preparing certain high internal phase water-in-oil emulsions. Such emulsions contain particular types of monomeric materials dissolved in the oil phase of the emulsion such that, when the emulsions are subjected to polymerization conditions, especially useful polymeric foam structures are realized. The specific emulsions which are prepared by the process herein are those which, when polymerized, provide foam structures that find particular utility for absorbing aqueous body fluids. These foams are thus suitable for use in absorbent products such as diapers and other incontinence management products.

BACKGROUND OF THE INVENTION

Water-in-oil emulsions having a relatively high ratio of water phase to oil phase are known in the art as high internal phase emulsions ("HIPEs" or "HIPE" emulsions). Continuous processes for preparing HIPE emulsions are disclosed, for example, in Lissant; U.S. Pat. No. 3,565,817; Issued Feb. 23, 1971 and Bradley et al; British Patent Application 2194166A; Published Mar. 2, 1988.

HIPE emulsions which contain polymerizable monomers in their external oil phase have been made and polymerized in order to study the geometric configuration of the oil and water phases of such emulsions. For example, Lissant and Mahan, "A Study of Medium and High Internal Phase Ratio Water/Polymer Emulsions," *Journal of Colloid and Interface Science*, Vol. 42, No. 1, January, 1973, pp. 201-208 discloses the preparation of water-in-oil emulsions which contain 90% internal water phase and which utilize styrene monomer in the oil phase. Such emulsions are prepared by subjecting the combined oil and water phases to agitation using an emulsifier and are subsequently polymerized to form a rigid porous structure having a cellular configuration determined by the phase relationship of its emulsion precursor.

Preparation of HIPE emulsions suitable for polymerization to porous structures, e.g., foams, useful for carrying and/or absorbing liquids are also known. For example, Barby et al, U.S. Pat. No. 4,797,310, Issued Jan. 10, 1989; Jones et al, U.S. Pat. No. 4,612,334; Issued Sep. 16, 1986; Haq et al, U.S. Pat. No. 4,606,958, Issued Apr. 19, 1986; and Barby et al, U.S. Pat. No. 4,522,953, Issued Jun. 11, 1989 all disclose porous polymeric materials which can be prepared from HIPE emulsions and which are useful for delivering liquids such as cleaning solutions to hard surfaces via products such as wipers and cleaning cloths.

The prior art has also recognized that the nature and characteristics of the porous polymeric foam materials formed by polymerizing HIPE emulsions is very much dependent on both the type of components which makeup the polymerizable HIPE emulsion and the process conditions used to form the emulsion. For example, Unilever, European Patent Application No. 60138, Published Sep. 15, 1982 discloses a process for preparing absorbent porous polymers (i.e., foams) from high internal phase emulsions comprising at least 90% by weight of water with the oil phase containing polymerizable monomers, surfactant and a polymerization catalyst. Edwards et al, U.S. Pat. No. 4,788,225, Issued Nov. 29, 1988 discloses the preparation of porous polymer materials which are rendered elastic by selecting certain monomer types (styrene, alkyl(meth)acrylates, crosslinker) and by using certain processing conditions to control the cell size of the eventually resulting porous polymer. Unilever, European Patent Application EP-A-299,762, Published Jan. 18, 1989 discloses that the use of an electrolyte in the water phase of polymerizable HIPE emulsions can affect the size of the openings between cells of the eventually resulting porous polymeric foam material.

Notwithstanding the fact that the existence and synthesis of polymerizable HIPE emulsions is known in the art, preparation of HIPE emulsions suitable for polymerization to useful absorbent foam material is not without its difficulties. Such HIPE emulsions, and especially HIPE emulsions having a very high ratio of water phase to oil phase, tend to be unstable. Very slight variations in monomer/crosslinker content in the emulsion, emulsifier selection, emulsion component concentrations, and temperature and/or agitation conditions can cause such emulsions to "break" or to separate to at least some degree into their distinct water and oil phases. Even if stable emulsions can be realized, alterations in emulsion composition and processing conditions can significantly affect the properties and characteristics of the eventually realized polymeric foam materials, thereby rendering such foam materials either more or less useful for their intended purpose. Such HIPE emulsion preparation difficulties can become even more troublesome when there is a need to produce polymerizable emulsions via a continuous process on an industrial or pilot plant scale in order to provide commercially useful or developmental quantities of polymeric absorbent foam materials.

Given the foregoing considerations, it is an object of the present invention to provide a process for preparing certain types of high internal phase emulsions that can be polymerized to form foam materials especially useful as an absorbent for aqueous body fluids, i.e., foams which are useful in absorbent products such as diapers.

It is a further object of the present invention to provide such a HIPE emulsion preparation process which can be carried out on a continuous basis.

It is a further object of the present invention to provide such a continuous HIPE emulsion preparation process which can be operated on a commercially meaningful scale.

SUMMARY OF THE INVENTION

The present invention provides a continuous process for the preparation of certain types of high internal phase emulsions that are themselves suitable for subsequent polymerization into absorbent foam materials. This process comprises the steps of:

Providing separate water phase and oil phase liquid feed streams as hereinafter defined;

Simultaneously introducing these liquid feed streams into a dynamic mixing zone at flow rates such that the water to oil weight ratio of liquid introduced ranges from about 2:1 to 10:1;

Subjecting the combined water and oil phase feed streams to sufficient shear agitation in the dynamic mixing zone to at least partially form an emulsified mixture therein while maintaining steady, non-pulsating flow rates for the oil and water phase streams;

Steadily increasing the water to oil weight ratio of the feed streams fed to the dynamic mixing zone to a value of from about 12:1 to 100:1 at a rate of increase that does not break the emulsion in the dynamic mixing zone, while maintaining certain conditions in the dynamic mixing zone as hereinafter described;

Continuously withdrawing emulsified contents of the dynamic mixing zone and continuously feeding these contents into a static mixing zone wherein they are subjected to additional shear agitation suitable for forming a stable high internal phase emulsion having a water-to-oil ratio of from about 12:1 to 100:1; and Continuously withdrawing the stable high internal phase emulsion from the static mixing zone so that it can be polymerized into a solid absorbent foam material.

In such a process, the liquid feed stream of the oil phase comprises from about 3 to 41 weight percent of a substantially water-insoluble, monofunctional glassy monomer component; from about 27 to 73 weight percent of a substantially water-insoluble, monofunctional rubbery comonomer component; from about 8 to 30 weight percent of a substantially water-insoluble, polyfunctional cross-linking agent component and from about 2 to 33 weight percent of an emulsifier component which is soluble in the oil phase and which is suitable for forming a stable water-in-oil emulsion. The liquid feed stream of the water phase comprises an aqueous solution containing from about 0.2% to 40% by weight of a water-soluble electrolyte.

As and after the water to oil weight ratio is increased by altering the rates at which the feed streams are introduced into the dynamic mixing zone, the emulsified contents of the dynamic mixing zone are maintained at a temperature of from about 250° C. to 700° C. Furthermore, the emulsified contents of the dynamic mixing zone are also subjected to continued shear agitation which is sufficient to eventually form a high internal phase emulsion that, upon subsequent polymerization, provides a foam material having an average cell size of from about 5 to 100 microns. The absorbent foams formed by polymerizing the emulsion prepared by the process herein will have these average cell size characteristics and will be especially suitable for use in absorbing aqueous body fluids.

DETAILED DESCRIPTION OF THE INVENTION

Figure 1:
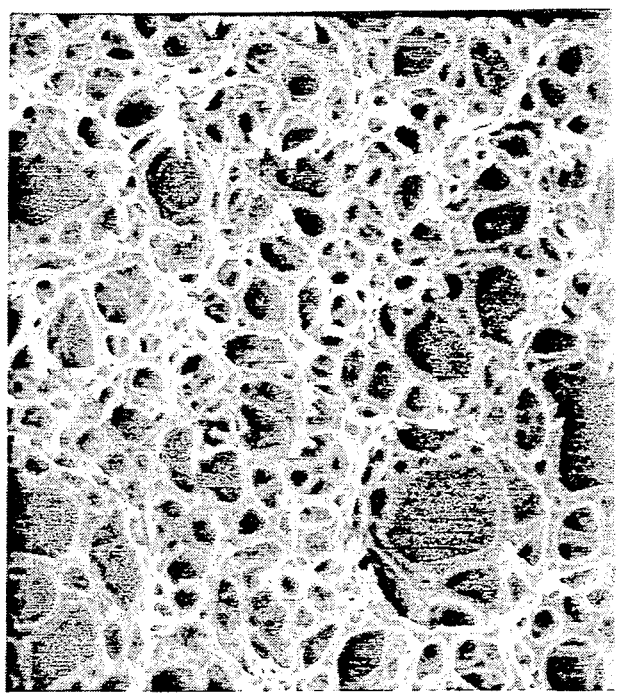
FIG. 1 of the drawings is a photomicrograph of the interstices of a polymerized HIPE emulsion of the type produced by the process of the present invention.

The emulsions which are prepared via the process of the present invention are water-in-oil emulsions having therein a relatively high ratio of water phase to oil phase. As indicated hereinbefore, emulsions of this type which have these relatively high water to oil phase ratios are known in the art as high internal phase emulsions (i.e., "HIPEs" or "HIPE" emulsions). HIPE emulsions having the oil and water phase characteristics of the present invention are suitable for polymerization (and dewatering) into foam materials which are especially useful as absorbents for aqueous body fluids.

Each of the essential steps used to prepare HIPE emulsions of this type via a continuous process is described in detail as follows:

A) Provision of the Oil Phase Feed Stream

The particular oil phase incorporated into the HIPE emulsions prepared by the process of this invention comprises monomers which polymerize to form a solid foam structure when the emulsions made from such an oil phase are eventually subjected to polymerization conditions. The monomers essentially utilized in this oil phase include a principal monomer component, a comonomer component and a cross-linking agent component. Selection of particular types and amounts of monofunctional principal monomer(s) and comonomer(s) and polyfunctional cross-linking agent(s) can be important to the realization of absorbent HIPE-based foam materials having the desired combination of properties which render such foam materials suitable for use as absorbents for body fluids.

The principal monofunctional monomer component utilized in the oil phase used to prepare the HIPE emulsions herein comprises one or more monomers that tend to impart glass-like properties to the eventually resulting foam structure. Such monomers are hereinafter referred to as "glassy" monomers, and are, for purposes of this invention, defined as monomeric materials which would produce high molecular weight (greater than 6000) homopolymers having a glass transition temperature, $T_g$, above about 40° C. The preferred monofunctional glassy monomer type is a styrene-based monomer with styrene itself being the most preferred monomer of this kind. Substituted, e.g., monosubstituted, styrene such as p-methylstyrene may also be employed. The monofunctional glassy monomer component will normally comprise from about 3% to 41%, more preferably from about 7% to 40% by weight of the oil phase used to form the HIPE emulsions herein.

Along with the principal glassy monomer material, a monofunctional comonomer component will also be present in the oil phase used in the instant HIPE emulsion preparation process. Such a monofunctional comonomer component comprises one or more comonomers which tend to impart rubber-like properties to the foams which eventually result from the polymerization of the emulsions prepared herein. Such comonomers are hereinafter referred to as "rubbery" comonomers and are, for purposes of this invention, defined as monomeric materials which would produce high molecular weight (greater than 10,000) homopolymers having a glass transition temperature, $T_g$, of about 40° C. or lower. Monofunctional rubbery comonomers of this type include, for example, alkylacrylates, alkylmethacrylates, allylacrylate, butadiene, substituted butadienes, vinylidine halides and combinations of such comonomers and comonomer types. Preferred rubbery comonomers include butylacrylate, 2-ethylhexylacrylate, butadiene, isoprene and combinations of these comonomers. Of all of these species, butylacrylate and 2-ethylhexylacrylate are the most preferred. The monofunctional rubbery comonomer component will generally comprise from about 27% to 73%, more preferably from about 27% to 66%, by weight of the oil phase used to form the HIPE emulsions herein.

Within the oil phase used to prepare the HIPE emulsions herein, both the monofunctional glassy principal monomer(s) and the monofunctional rubbery comonomer(s) must be present within the hereinbefore recited concentration ranges. In addition, the molar ratio of monofunctional glassy monomer component to the monofunctional rubbery component in the oil phase will generally range from about 1:25 to 1.5:1, more preferably from about 1:9 to 1.5:1.

Since the polymer chains formed from the glassy monomer(s) and the rubbery comonomer(s) are to be cross-linked when the emulsions prepared herein are subsequently polymerized, the oil phase must also contain a polyfunctional cross-linking agent. As with the monofunctional monomers and comonomers, selection of a particular type and amount of cross-linking agent can be very important to the eventual realization of HIPE emulsions which are polymerizable to foams having the desired combination of structural, mechanical, and fluid-absorbing properties.

Depending upon the type and amounts of monofunctional monomers and comonomers utilized, and depending further upon the desired characteristics of the eventually realized polymeric foams, the polyfunctional cross-linking agent component for use in the oil phase can be selected from a wide variety of polyfunctional, preferably difunctional, monomers. Thus, the cross-linking agent may be a divinyl aromatic material such as divinylbenzene, divinyltolulene or diallylphthalate. Alternatively, divinyl aliphatic cross-linkers such as any of the diacrylic acid esters of polyols can be utilized. The cross-linking agent found to be suitable for preparing the most acceptable foam-forming HIPE emulsions herein is divinylbenzene.

The cross-linking agent of whatever type will generally be employed in the oil phase used in the emulsion-forming process herein in an amount of from about 8% to 40%, more preferably from about 10% to 25%, by weight. Amounts of cross-linking agent(s) within such ranges will generally provide a cross-linker molar concentration of from about 5 mole percent to about 60 mole percent, based on total monomers present in the oil phase.

The major portion of the oil phase used to prepare the HIPE emulsions herein will comprise the aforementioned monomers, comonomers and cross-linking agents which eventually form the polymeric foam absorbents. It is therefore essential that these monomers, comonomers and cross-linking agents be substantially water-insoluble so that they are primarily soluble in the oil phase and not the water phase of the emulsions herein. Use of such substantially water-insoluble monomer materials ensures that HIPE emulsions of appropriate characteristics and stability will be realized.

It is, of course, preferred that the monomers, comonomers and cross-linking agents used to form the foam precursor emulsions herein be of the type such that the eventually formed foam polymer is suitably non-toxic and sufficiently chemically stable. Thus such monomers, comonomers and cross-linking agent should preferably have little or no toxicity in the very low residual concentrations wherein they may be encountered during post-polymerization foam processing and/or use.

Another essential component of the oil phase used to form the HIPE emulsions in accordance with the present invention comprises an emulsifier which permits formation of stable HIPE emulsions. Such emulsifiers are those which are soluble in the oil phase used to form the emulsion. Emulsifiers utilized may be nonionic, cationic, anionic or amphoteric provided the emulsifier or combination of emulsifiers will form a stable HIPE emulsion. Preferred types of emulsifiers which can be used to provide an emulsifier component having suitable characteristics include the sorbitan fatty acid esters, polyglycerol fatty acid esters, polyoxyethylene (POE) fatty acids and esters. Especially preferred are the sorbitan fatty acid esters such as sorbitan monolaurate (SPAN ® 20), sorbitan monooleate (SPAN ® 80) and combinations of sorbitan trioleate (SPAN ® 85) and sorbitan monooleate (SPAN ® 80). One such particularly preferred emulsifier combination comprises the combination of sorbitan monooleate and sorbitan trioleate in a weight ratio greater than or equal to about 3.1, more preferably about 4:1. Other operable emulsifiers include TRIODAN ® 20 which is a commercially available polyglycerol ester marketed by Grindsted and EMSORB 2502 which is a sorbitan sesquioleate marketed by Henkel.

The emulsifier component will generally comprise from about 2% to 33% by weight of the oil phase used to form the HIPE emulsions herein which in turn are used to prepare polymeric absorbent foams. More preferably, the emulsifier component will comprise from about 4% to 25% by weight of the oil phase.

In addition to the monomeric and emulsifier components hereinbefore described, the oil phase used to form polymerizable HIPE emulsions herein may also contain additional optional components. One such optional oil phase component may be an oil soluble polymerization initiator of the general type hereinafter described. Another possible optional component of the oil phase may be a substantially water insoluble solvent or carrier for the oil phase monomer, cross-linker and/or emulsifier components. A solvent or carrier of this type must, of course, not be capable of dissolving the eventually polymerized monomers. Use of such a solvent is not preferred, but if such a solvent or carrier is employed, it will generally comprise no more than about 10% by weight of the oil phase.

The oil phase, as hereinbefore described, may itself be prepared in any suitable manner by combining the essential and optional components using conventional techniques. Such a combination of components may be carried out in either continuous or batch-wise fashion using any appropriate order of component addition. The oil phase so prepared will generally be formed and stored in a feed tank, from which tank the oil phase can be provided in a liquid feed stream of any desired flow rate as hereinafter described.

B) Provision of the Water Phase Feed Stream

As indicated, an oil phase as hereinbefore described is the continuous external phase in the HIPE emulsions to be polymerized to realize absorbent foams. The discontinuous internal phase of such polymerizable HIPE emulsions is a water phase which will generally be an aqueous solution containing one or more dissolved components. Like the oil phase, the water phase used to form the HIPE emulsions herein will be fed to the process as a separate stream.

One essential dissolved component of the water phase is a water-soluble electrolyte. The dissolved electrolyte in the water phase used to form the HIPE emulsions herein serves to minimize the tendency of monomers and crosslinkers which are primarily oil soluble to also dissolve in the water phase. This, in turn, can minimize the extent to which, during subsequent polymerization of the emulsion, polymeric material fills the cell windows at the oil/water interfaces formed by the water phase bubbles. Thus the presence of electrolyte and the resulting ionic strength of the water phase can determine whether and to what degree the eventually resulting polymeric foams may be open-celled.

Any electrolyte which provides ionic species to impart ionic strength to the water phase may be used. Preferred electrolytes are mono-, di-, or tri-valent inorganics salts such as the water-soluble halides (e.g., chlorides), nitrates and sulfates of alkali metals and alkaline earth metals. Examples include sodium chloride, calcium chloride, sodium sulfate and magnesium sulfate. Calcium chloride is the most preferred electrolyte for use in the water phase.

Generally electrolyte will be present in the water phase used to form the HIPE emulsions in a concentration which ranges from about 0.2% to about 40% by weight of the water phase. More preferably, the electrolyte will comprise from about 0.5% to 20% by weight of the water phase.

The HIPE emulsions formed via the process herein will, in addition to the essential oil and water phase components hereinbefore described, also typically contain a polymerization initiator. Such an initiator component will generally be added to the water phase used to form the HIPE emulsions and can be any conventional water-soluble free radical initiator. Materials of this type include peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts.

The initiator material can comprise up to about 5 mole percent based on the total moles of polymerizable monomers present in the oil phase. More preferably, the initiator comprises from about 0.001 to 0.5 mole percent based on the total moles of polymerizable monomers (i.e., monomers, comonomers, cross-linkers) in the oil phase. When used in the water-phase, such initiator concentrations can be realized by adding initiator to the water phase to the extent of from about 0.02% to 0.4%, more preferably from about 0.1% to 0.2% by weight of the water phase.

As with the oil phase, the water phase, containing the essential and optional components hereinbefore described, may itself be prepared by combining these components in conventional manner. Thus, the water phase may be prepared in either continuous or batch-wise fashion using any appropriate order of addition of water phase components. As with the oil phase, the water phase will generally be prepared and stored in a separate feed tank which is equipped with means for delivering a water phase liquid stream from this tank at any desired flow rate.

C) Initial Introduction of Oil and Water Phase Feed Streams Into the Dynamic Mixing Zone The liquid streams of both oil and water phases as hereinbefore described are initially combined by simultaneously introducing liquid feed streams of both these phases together into a dynamic mixing zone. This dynamic mixing zone, and the emulsion-forming agitation imparted to the liquid contents thereof, are hereinafter described in greater detail.

During this stage of initial combination of liquid feed streams of the oil and water phases, flow rates of these feed streams are set so that the weight ratio of water phase to oil phase being introduced into the dynamic mixing zone is well below that of the HIPE emulsions which are to be eventually realized. In particular, flow rates of the oil and water phase liquid streams are set such that the water to oil weight ratio during this initial introduction stage ranges from about 2:1 to 10:1, more preferably from about 2.5:1 to 5:1. The purpose of combining the oil and water phase streams at these relatively low water to oil ratios is to permit formation in the dynamic mixing zone of at least some amount of a water-in-oil emulsion which is relatively stable and does not readily "break" under conditions encountered in the dynamic mixing zone.

The actual flow rates of the oil and water phase liquid feed streams during this stage of the initial introduction into the dynamic mixing zone will vary depending upon the scale of the emulsion preparation process desired. For pilot plant scale operations, the oil phase flow rate during this initial introduction stage can range from about 0.02 to 0.2 liter/minute, and the water phase flow rate can range from about 0.04 to 2.0 liters/minute. For commercial scale operations, the oil phase flow rate during this initial introduction stage can range from about 10 to 25 liters/minute, and the water phase flow rate can range from about 20 to 250 liters/minute.

For the initial startup of the process herein, the dynamic mixing zone is filled with oil and water phase liquid before agitation begins. During this filling stage, gas is vented from the dynamic mixing zone. Before agitation begins, the liquid in the dynamic mixing zone is in two separate phases, i.e., an oil phase and a water phase. Once the dynamic mixing zone is filled with liquid, agitation is begun as described in greater detail hereinafter, and emulsion begins to form in the dynamic mixing zone. At this point, oil and water phase flow rates should be set within the ranges hereinbefore set forth to provide the relatively low initial water to oil weight ratio within the range which is also hereinbefore set forth.

D) Initial Emulsion Formation in the Dynamic Mixing Zone

As noted, the oil and water phase feed streams are initially combined by means of their simultaneous introduction into a dynamic mixing zone. For purposes of the present invention, the dynamic mixing zone comprises a containment vessel for liquid components, which vessel is equipped with means for imparting shear agitation to the liquid contents of the vessel. Such shear agitation means must be suitable for providing agitation or mixing beyond that which arises by virtue of simple flow of liquid material through the containment vessel.

The agitation means which is employed as an element of the dynamic mixing zone can comprise any conventional apparatus which imparts the requisite amount of shear agitation to the liquid contents of the dynamic mixing zone. One suitable type of agitation apparatus is a pin impeller which comprises a cylindrical shaft from which a number of rows (flights) of cylindrical pins extend radially. The number, dimensions, and configuration of the pins on the impeller shaft can vary widely, depending upon the amount of shear agitation which the impeller is to impart to the dynamic mixing zone liquid contents. As discussed more fully hereinafter with respect to the drawing, a pin impeller of this type can be mounted within a generally cylindrical mixing vessel which serves as the dynamic mixing zone. The impeller shaft is positioned generally parallel to the direction of liquid flow through the cylindrical dynamic mixing zone. Shear agitation is provided by rotating the impeller shaft at a speed which imparts the requisite degree of shear agitation to the liquid material passing through the dynamic mixing zone.

The shear agitation imparted to the liquid contents which have been initially introduced into the dynamic mixing zone is that which is sufficient to form at least some of the dynamic mixing zone contents into a water-in-oil emulsion having water to oil ratios within the ranges set forth hereinbefore. Frequently such shear agitation at this point will range from about 1000 to 7000 sec.$^{-1}$, more preferably, from about 1500 to 3000 sec.$^{-1}$. The amount of shear agitation need not be constant but may be varied over the time needed to effect such emulsion formation. As indicated, not all of the water and oil phase material which has been introduced into the dynamic mixing zone at this point need be incorporated into the water-in-oil emulsion so long as at least some emulsion of this type (e.g., the emulsion comprises at least about 90% by weight of the liquid effluent from the dynamic mixing zone) is formed in and flows through the dynamic mixing zone.

Once agitation begins, it is important that both the oil and water phase flow rates be steady and non-pulsating. This is because sudden or precipitous changes in these flow rates can cause the emulsion that has been formed in the dynamic mixing zone to break. Accordingly, changes in flow rates of the oil and/or water phases should be gradual enough to prevent any significant separation of the emulsion which has formed in the dynamic mixing zone into non-emulsified oil and water phases.

E) HIPE Formation in the Dynamic Mixing Zone

After a water-in-oil emulsion of relatively low water-to-oil ratio has been formed in the dynamic mixing zone by selection of suitable flow rates and shear agitation conditions as hereinbefore described, steps are taken to convert the emulsion so formed, along with the additional non-emulsified contents of the dynamic mixing zone, into a high internal phase emulsion, e.g., a HIPE. This is accomplished by altering the relative flow rates of the water and oil phase streams being fed into the dynamic mixing zone. Thus, such an increase in water-to-oil ratio of the phases being introduced can be accomplished by increasing the water phase flow rate, by decreasing the oil phase flow rate or by a combination of these steps. The water-to-oil ratios to be eventually realized by such an adjustment of the water phase and/or oil phase flow rates will generally range from about 12:1 to 100:1, more preferably from about 20:1 to 70:1, most preferably from about 25:1 to 50:1.

Adjustment of the oil phase and/or water phase flow rates to increase the water to oil phase ratio of the liquid material being fed to the dynamic mixing zone can begin immediately after initial formation of emulsion in the dynamic mixing zone. This will generally occur soon after agitation is begun in the dynamic mixing zone. The length of time taken to increase the water to oil ratio to the ultimately desired higher ratio will depend on the scale of the process being carried out and the magnitude of the eventual water to oil ratio to be reached. Frequently the duration of the flow rate adjustment period needed to increase water to oil ratios will range from about 1 to 5 minutes.

In altering the relative water and oil phase flow rates to achieve the ultimately desired relatively high water-to-oil ratios for HIPE emulsion preparation, care should be taken to approach these desired ratios gradually. As noted hereinbefore, sudden or precipitous changes in the water phase and/or oil phase flow rates can cause the emulsion in the dynamic mixing zone to "break" before or shortly after the requisite HIPE emulsions can be formed. The actual rate of increase of the water-to-oil ratio in the streams being fed to the dynamic mixing zone will be dependent upon the particular components of the emulsion being prepared as well as the scale of the process being carried out. For any given HIPE formula and process setup, emulsion stability can be controlled by simply monitoring the nature of the effluent from the process to ensure that it comprises at least some material (e.g., at least 90% of the total effluent) in substantially HIPE emulsion form.

Conditions within the dynamic mixing zone during emulsion formation can also affect the nature of the HIPE emulsion (and ultimately the polymerized absorbent foam made therefrom) which is prepared by the process herein. One element of dynamic mixing zone conditions which can impact on the character of HIPE produced is the temperature of the emulsion components within the dynamic mixing zone. Generally the emulsified contents of the dynamic mixing zone should be maintained at a temperature of from about 25° to 70° C., more preferably from about 35° to 650° C., during the HIPE formation step.

Another element of the dynamic mixing zone conditions involves the amount of shear agitation imparted to the contents of the dynamic mixing zone both during and after adjustment of the water and oil phase flow rates to form the HIPE-ratio emulsions herein. The amount of shear agitation imparted to the emulsified material in the dynamic mixing zone will directly impact on the size of the cells which make up the eventually-realized absorbent foam material. For a given set of emulsion component types and ratios, and for a given combination of flow rates into the dynamic mixing zone, subjecting the dynamic mixing zone liquid contents to greater amounts of shear agitation will tend to reduce the size of the cells in the absorbent foam material produced from the HIPE emulsions eventually realized herein.

Foam cells, and especially cells which are formed by polymerizing a monomer-containing oil phase that surrounds relatively monomer-free water-phase bubbles, will frequently be substantially spherical in shape. The size or "diameter" of such substantially spherical cells is thus a commonly utilized parameter for characterizing foams in general as well as for characterizing absorbent foams of the type prepared from the HIPE emulsions made via the process of the present invention. Since cells in a given sample of polymeric foam will not necessarily be of approximately the same size, an average cell size, i.e., average cell diameter, will often be specified.

A number of techniques are available for determining average cell size in foams. These techniques include mercury porosimetry methods which are well known in the art. The most useful technique, however, for determining cell size in foams involves simple photographic measurement of a foam sample. FIG. 1 of the drawing, for example, is a photomicrograph of a fracture surface of a typical foam absorbent structure prepared from a HIPE emulsion made by the process herein. Superimposed on the photomicrograph is a scale representing a dimension of 10 microns. Such a scale can be used to determine average cell size via an image analysis procedure. Image analysis of photomicrographs of foam samples is, in fact, a commonly employed analytical tool which can be used to determine average cell size of foam structures. Such a technique is described in greater detail in Edwards et al; U.S. Pat. No. 4,788,225; Issued Nov. 29, 1988. This patent is incorporated herein by reference.

For purposes of the present invention, average cell size in foams made by polymerizing HIPE emulsions prepared herein can be used as a means for quantifying the amount of shear agitation imparted to the emulsified contents in the dynamic mixing zone during the instant process. In particular, after the oil and water phase flow rates have been adjusted to provide the requisite HIPE water/oil ratio, the emulsified contents of the dynamic mixing zone should be subjected to shear agitation which is sufficient to eventually form a HIPE emulsion that, upon subsequent polymerization, provides a foam having an average cell size of from about 5 to 100 microns. More preferably, such agitation will be that suitable to realize an average cell size in the subsequently formed foam of from about 10 to 90 microns. This will typically amount to shear agitation of from about 1000 to 7000 sec.$^{-1}$, more preferably from about 1500 to 3000 sec.$^{-1}$.

As with the shear agitation utilized upon initial introduction of the oil and water phases into the dynamic mixing zone, shear agitation to provide HIPE emulsions need not be constant during the process. For example, impeller speed can be increased or decreased during the HIPE preparation process as desired or required to provide emulsions which form foams having the particular desired average cell size characteristics hereinbefore specified.

F) Transfer of Dynamic Mixing Zone Effluent to Static Mixing Zone

In the process of the present invention, the emulsion-containing liquid contents of the dynamic mixing zone are continuously withdrawn from the dynamic mixing zone and introduced into a static mixing zone wherein they are subjected to further mixing and agitation. The nature and composition of the effluent from the dynamic mixing zone will, of course, change over time as the process herein proceeds from initial startup to initial emulsion formation in the dynamic mixing zone to HIPE emulsion formation in the dynamic mixing zone, as the water-to-oil ratio is increased. During the initial startup procedure, the dynamic mixing zone effluent may contain little or no emulsified material at all. After emulsion formation begins to occur in the dynamic mixing zone, the effluent therefrom will comprise a water-in-oil emulsion having a relatively low water-to-oil ratio, along with excess oil and water phase material which has not been incorporated into the emulsion. Finally, after the water-to-oil ratio of the two feed streams into the dynamic mixing zone has been increased, the dynamic mixing zone effluent will primarily comprise a HIPE emulsion along with relatively small amounts of oil and water phase materials which have not been incorporated into this HIPE emulsion.

Once steady state operation is achieved, the flow rate of effluent from the dynamic mixing zone, which becomes the feed stream to the static mixing zone, will equal the sum of the flow rates of the water and oil phases being introduced into the dynamic mixing zone. After water and oil flow rates have been properly adjusted to provide formation of the desired HIPE emulsion, the effluent flow rate from the dynamic mixing zone will typically range from about 35 to 800 liters per minute for commercial scale operations. For pilot plant scale operations, dynamic mixing zone effluent flow rates will typically range from about 0.8 to 9.0 liters per minute.

The effluent continuously withdrawn from the dynamic mixing zone is continuously introduced into a static mixing zone for further processing. The static mixing zone provides resistance to flow of liquid material through the process operations herein and thus provides back pressure for the liquid contents of the dynamic mixing zone. However, the primary purpose of the static mixing zone in the present process is to to subject the emulsified material from the dynamic mixing zone to additional agitation and mixing in order to complete the formation of the desired stable HIPE emulsion.

For purposes of the present invention, the static mixing zone can comprise any suitable containment vessel for liquid materials, which vessel is internally configured to impart agitation or mixing to such liquid materials as these materials flow through the vessel. A typical static mixer is a spiral mixer which can comprise a tubular device having an internal configuration in the form of a series of helices that reverse direction every 180° of helical twist. Each 180° twist of the internal helical configuration is called a flight. Typically, a static mixer having from 12 to 32 helical flights which intersect at 90° angles will be useful in the process herein.

In the static mixing zone, shear forces are imparted to the liquid material therein simply by the effect of the internal configuration of the static mixing device on the liquid as it flows through the device. Typically such shear is imparted to the liquid contents of the static mixing zone to the extent of from about 100 to 7000 sec.$^{-1}$, more preferably from about 500 to 3000 sec.$^{-1}$.

In the static mixing zone, essentially all of the water and oil phase material which has not been incorporated into the emulsified material in the dynamic mixing zone will, after HIPE water/oil ratios are achieved, be formed into a stable HIPE emulsion. Typically such a HIPE emulsion will have a water-to-oil phase ratio which ranges from about 12:1 to 100:1, more preferably from about 20:1 to 70:1. Such emulsions are stable in the sense that they will not significantly separate into their water and oil phases, at least for a period of time sufficient to permit polymerization of the monomeric contents of the oil phase therein.

G) Polymerizable HIPE Emulsion From the Static Mixing Zone

Emulsified material can be continuously withdrawn from the static mixing zone at a rate which approaches or equals the sum of the flow rates of the water and oil phase streams fed to the dynamic mixing zone. After the water-to-oil ratio of the feed materials has been increased to within the desired HIPE range and steady state conditions have been achieved, the effluent from the static mixing zone will essentially comprise a stable HIPE emulsion suitable for further processing into absorbent foam material.

The stable HIPE emulsions having the particular composition hereinbefore specified can be converted to useful absorbent foam materials by subjecting these HIPE emulsion materials to suitable polymerization and dewatering conditions. In this manner, the monomeric materials present in the external oil phase of the stable HIPE water-in-oil emulsions will polymerize to form a solid polymeric structure in the form of a cellular foam. The polymeric foam structure formed by polymerization of the particular HIPE emulsions produced by the process therein are those which are relatively open-celled. This means that the individual cells of the resulting foam are, for the most part, not completely isolated from each other by polymeric material filling the cell walls. Thus the cells in such substantially open-celled foam structures have intercellular openings or "windows" which are large enough to permit ready fluid transfer from one cell to the other within the foam structure. This renders such foams especially useful as fluid absorbents.

In substantially open-celled structures of the type which can be prepared from the HIPE emulsions produced by the instant invention, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 1.

Polymerization of the HIPE emulsions herein to form absorbent foams can be brought about by placing the HIPE emulsion in a suitable polymerization container and by subjecting the emulsion therein to curing conditions. Such curing conditions can comprise maintenance of a temperature from about 55° to 90° C. for a period of from about 4 to 24 hours. The foam materials so produced will generally also be subsequently processed to render them suitable for use as fluid absorbents. Subsequent processing steps may include, for example, a) washing of the foam structure to remove residual water phase material from the cells of the foam, b) treating the foam structure with hydrophilizing agents to render the foam internal surfaces more suitable for absorbing hydrophilic liquids such as aqueous body fluids, c) dewatering by compression and/or heating to remove residual water therefrom to the point such foams will be effective as absorbents for aqueous body fluids, and/or d) cutting or other shaping techniques to provide the foam material in suitable form for incorporation into absorbent products. The absorbent foam materials which can be prepared from the HIPE emulsions prepared by the process herein are described in greater detail in the U.S. patent application of DesMarais, Stone, Thompson, Young, LaVon, and Dyer having Ser. No. 07/743,839, (P&G Case No. 4451) filed Aug. 12, 1991. This application is incorporated herein by reference.

APPARATUS

The continuous HIPE emulsion preparation process herein can be carried out using conventional liquid processing equipment and apparatus. A typical arrangement of such equipment and apparatus is illustrated by the schematic flow diagram set forth as FIG. 2 of the drawing.

Figure 2:
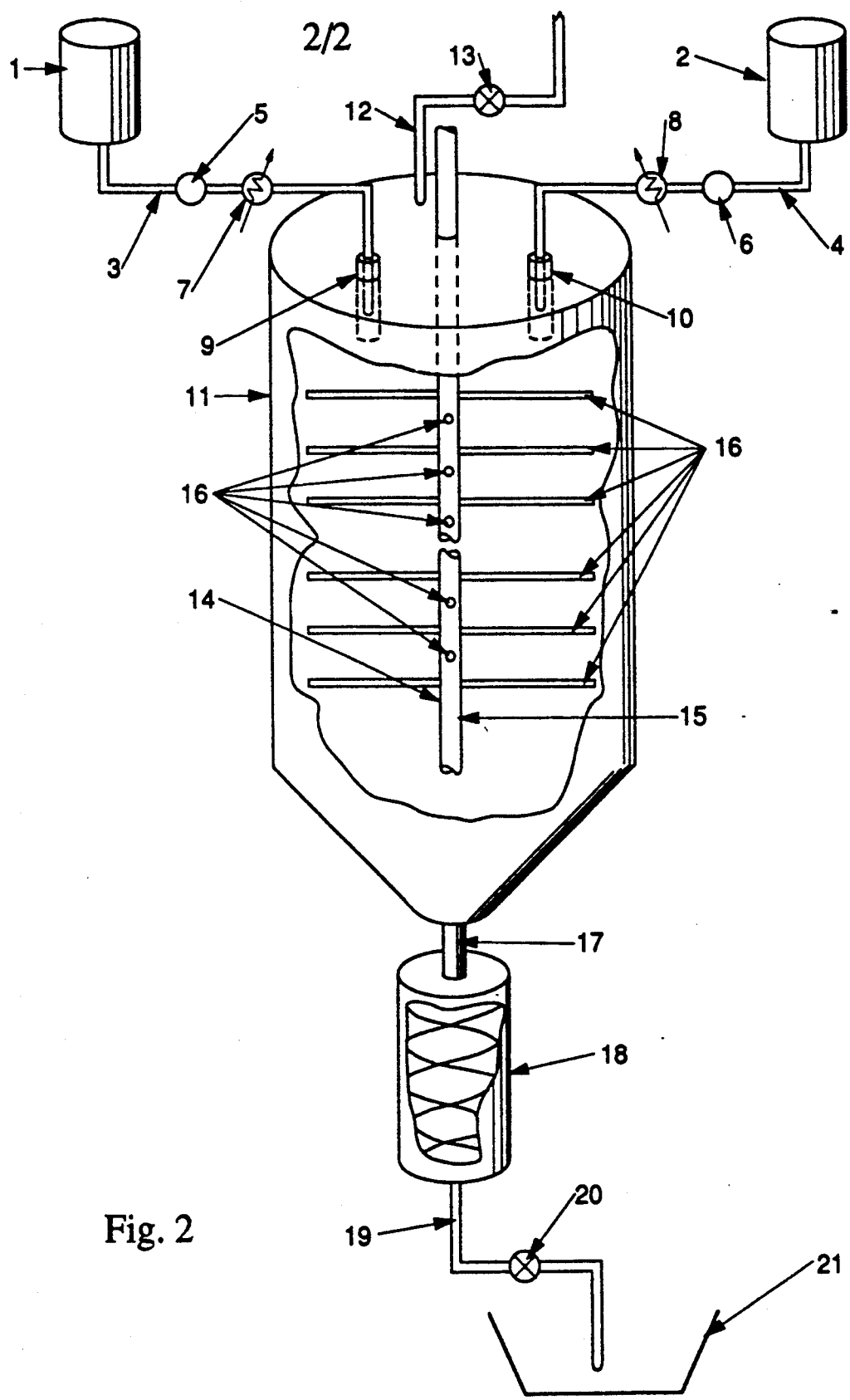
FIG. 2 of the drawings is a schematic flow diagram showing an arrangement of apparatus and equipment which can be used for carrying out the process of the present invention.

As shown in FIG. 2, the equipment useful for carrying out the process herein can comprise an oil phase feed tank 1 and a water phase feed tank 2. Oil phase liquid is fed via oil phase feed line 3, through an oil phase feed pump 5, an oil phase heat exchanger 7 and an oil phase metering tube 9 into a dynamic mixing vessel 11. Similarly, water phase liquid material is fed via water phase feed line 4 through a water phase feed pump 6, a water phase heat exchanger 8 and a water phase metering tube 10 into the dynamic mixing vessel 11.

The dynamic mixing vessel 11 is fitted with a vent line 12. Venting of air from the dynamic mixing vessel is controlled by a vent valve 13. Venting is required during the filling of the vessel and may be carried out as needed to maintain an all-liquid environment in the dynamic mixing vessel 11. The metering tubes 9 and 10 are required to insure steady stream flow of the oil and water phases into the mixer and should be sized to give a pressure differential between the feed lines and the mixing vessel of about 13.8 kPa (2 PSI) at the intended process flow rate.

The dynamic mixing vessel 11 is also fitted with a pin impeller 14. The pin impeller itself comprises a shaft 15 which holds a number, e.g., 16 or 17, of flights of cylindrical impeller pins 16 protruding radially outwards from the impeller shaft. These flights of impeller pins are positioned in four rows which run along a portion of the length of the impeller shaft with the rows positioned at 90° angles around the circumference of the impeller shaft. The rows of impeller pins are offset along the length of the impeller shaft such that flights which are perpendicular to each other are not in the same radial plane extending from the axis of the shaft. The impeller 14 is used to impart shear agitation to the liquid contents of the dynamic mixing vessel 11 in order to form emulsified material in this dynamic mixing vessel. Such emulsified material is withdrawn from the dynamic mixing vessel 11 via the dynamic mixer effluent line 17, and is fed thereby into a static mixing vessel 18.

Emulsified liquid material is subjected to further agitation or mixing in the static mixing vessel 18 and is withdrawn therefrom via a static mixer effluent line 19. Such effluent, when in the form of a stable HIPE emulsion, can be removed via effluent line 19 and a static mixer effluent valve 20 into a suitable polymerization container 21. Stable HIPE emulsion in polymerization container 21 can be subjected to polymerization conditions in order to form a desired absorbent foam material.

EXAMPLES

Preparation of high internal phase emulsions and their subsequent polymerization and dewatering into absorbent foam materials are illustrated by the following examples. The procedures set forth are in general carried out on a semi-pilot plant scale of operation using apparatus substantially similar to that hereinbefore described with respect to FIG. 2 of the drawing.

EXAMPLE I

Calcium chloride (320 g.) and potassium persulfate (48 g.) are dissolved in 32 liters of distilled water. This provides the water phase feed stream to be used in the following process for forming a HIPE emulsion.

To a monomer combination comprising styrene (420 g.), divinylbenzene (660 g.) and 2-ethylhexylacrylate (1920 g.) are added sorbitan monooleate (450 g. as SPAN® 80) and sorbitan trioleate (150 g. as SPAN® 85). After mixing, this comprises the oil phase feed stream to be used in the following process for forming a HIPE emulsion.

At liquid temperatures in the range of 55° C. to 650° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 18 cm in length with a diameter of about 1.9 cm. The shaft holds two rows of 17 and two rows of 16 cylindrical pins each having a diameter of 0.5 cm extending radially outward from the central axis of the shaft to a length of 1 cm. The four rows are positioned at 90° angles around the circumference of the impeller shaft with the rows that are perpendicular to each other being offset along the length of the shaft as shown in the drawing. The pin impeller is mounted in a cylindrical sleeve which forms the dynamic mixing apparatus, and the pins in the impeller have a clearance of 0.8 mm from the walls of the cylindrical sleeve. The impeller is operated at a speed of 900 revolutions per minute.

A static mixer (8 inches long by ¼ inch outside diameter by 0.190 inch inside diameter) with the helical internal configuration hereinbefore described is mounted downstream from the dynamic mixing apparatus to provide back pressure in the dynamic mixer. This helps keep the dynamic mixing apparatus comprising the cylindrical sleeve with its pin impeller full of liquid contents. The static mixer also helps to ensure appropriate and complete formation of a HIPE emulsion from the oil and water phases.

An emulsion having the eventually desired ratio of water to oil phases is approached gradually. At first, flow rates are adjusted so that 3 parts by weight of the water phase and 1 part by weight of the oil phase enter the dynamic mixing apparatus with the pin impeller. The water to oil phase ratio is increased, over a period of a few minutes, until a ratio of 12-13 parts water phase to 1 part oil phase is passing into the dynamic mixer, at a rate of 15 ml/sec. Gradually, the oil flow rate is decreased so that the water phase/oil phase weight ratio is near 25:1. At this stage, the viscosity of the emulsion flowing out of the static mixer drops. (Visually, the whitish mixture becomes more translucent at this point.)

The flow rate of the oil phase is thereafter further decreased to the point where the desired water phase/oil phase weight ratio of 30-33:1 is reached. Visually, the emulsion at this stage flows from the static mixer orifice with the consistency of a whipping cream and "sets" to a consistency reminiscent of a creamy yogurt.

At this point, the emulsion emerging from the static mixer is ready for curing. The emulsion is fed to a generally rectangular mold which is made of polyethylene and which has the dimensions, 38 cm length; 25 cm width and 22 cm depth. Emulsion is emptied into such molds until each mold contains approximately 20,000 ml of the emulsion to be cured.

Curing is effected by placing the emulsion-containing molds in a curing oven at a temperature of 60° C. for a period of about 16 hours. After curing, the resulting solid polymerized foam material contains up to 98% water and is soft and sopping wet to the touch.

The foam material at this point may be subjected to further processing to render it suitable for use as an absorbent for aqueous body fluids. Such further processing may involve washing of the foam to remove residual water and oil phase components, treatment of the foam with hydrophilizing agents to render its internal surfaces more hydrophilic and dewatering to provide substantially dry foam material.

When the foam material prepared as described herein is dried and subjected to photomicrographic image analysis in the manner hereinbefore described, it can be determined that such a foam material has an average cell size of about 40 microns.

EXAMPLE II

Another HIPE emulsion (and the subsequently resulting polymeric foam material made therefrom) is prepared in the same general manner as set forth hereinbefore in Example I. In this example, the emulsion preparation and polymerization procedures are carried out as in Example I but with the following differences in materials, concentrations and conditions:

1) An emulsifier mixture of 480 g of SPAN® 80 and 120 g of SPAN® 85 is used in the oil phase.
2) A 14 inch long × ⅜ inch O.D. (35.6 cm × 0.95 cm) static mixer is used downstream from the dynamic mixing apparatus.
3) The pin impeller in the dynamic mixer is operated at a speed of 850 revolutions per minute.
4) The final water to oil phase weight ratio of the HIPE emulsion produced is 31:1.
5) A curing temperature of 66° C. is used.

After drying as in Example I, the Example II foam is subjected to photomicrographic image analysis and is found to have an average cell size of 37 microns.

EXAMPLE III

This example illustrates the preparation of another type of HIPE emulsion (and the subsequently resulting polymer foam material made therefrom) falling within the scope of the present invention.

Calcium chloride (36.32 kg) and potassium persulfate (568 g) are dissolved in 378 liters of water. This provides the water phase stream to be used in a continuous process for forming a HIPE emulsion.

To a monomer combination comprising styrene (1600 g), divinylbenzene 55% technical grade (1600 g), and 2-ethylhexylacrylate (4800 g) is added sorbitan monolaurate (960 g as SPAN® 20). After mixing, this combination of materials is allowed to settle overnight. The supernatant is withdrawn and used as the oil phase in a continuous process for forming a HIPE emulsion. (About 75 g of a sticky residue is discarded.)

At an aqueous phase temperature of 48°-50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft, as described in Example I, holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are 15"×23"×9" (38.1 cm×58.4 cm×22.9 cm). These boxes are pretreated with a film of a solution comprising a 20% solution of SPAN ® 20 in an equal weight solvent mixture of xylene and isopropanol. The solvent mixture is allowed to evaporate to leave only the SPAN ® 20. Forty-seven liters of emulsion are collected in each box.

The emulsion-containing boxes are kept in a room maintained at 65° C. for 18 hours to bring about polymerization of the emulsion in the boxes to thereby form polymeric foam material. After curing is complete, the wet cured foam material is removed from the curing boxes.

The foam material at this point is subjected to further processing in order to dewater the foam and leave a residual amount of the CaCl$_2$ hydrophilizing agent incorporated within the foam structure. After such processing, the foam material has a residual water content of about 5-7% by weight of polymerized material (including water of hydration) and contains residual sorbitan monolaurate in an amount of about 11% by weight and hydrated calcium chloride in an amount of about 5% by weight (anhydrous basis).

Such a foam is of the "thin-until-wet" type meaning that such a foam will collapse to a relatively smaller caliper upon dewatering but will reexpand in caliper when it encounters and subsequently imbibes aqueous body fluids. The thin-until-wet foam material prepared according to this Example III will, in its expanded state, have an average cell size of about 15 microns.

EXAMPLE IV

This example illustrates the preparation of yet another type of HIPE emulsion (and the subsequently resulting thin-until-wet polymer foam material made therefrom) falling within the scope of the present invention.

Calcium chloride (36.32 kg.) and potassium persulfate (568 g) are dissolved in 378 liters of water. This provides the water phase stream to be used in the following process for forming a HIPE emulsion.

To a monomer combination comprising styrene (1600 g), divinylbenzene 55% technical grade (1600 g), and 2-ethylhexylacrylate (4800 g) is added sorbitan monolaurate (480 g as SPAN ® 20) and a mixture of sorbitan monolaurate and sorbitan monopalmitate (240 g of SPAN ® 20 and 240 g of SPAN ® 40) to facilitate dissolution of the SPAN ® 40. After mixing, this oil phase is allowed to settle overnight. The supernatent is withdrawn and used in the following process. About 75 g of a sticky residue is discarded.

At an aqueous phase temperature of 48°-50° C., and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm. in length with a diameter of about 1.9 cm. The shaft holds 4 rows of pins, two rows having 17 pins and two rows having 16 pins, each having a diameter of 0.5 cm. extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer (14 in. long by ½ in. outside diameter, a TAH Industries model 070-821, modified by cutting off 2.4 inches) is mounted downstream from the dynamic mixing apparatus to provide back pressure in the dynamic mixer and provide uniformity in the emulsion.

The combined mixing apparatus is filled with oil phase and water phase at a ratio of 2 parts water to 1 part oil, while venting the apparatus to allow air to escape while filling the apparatus completely. The flow rates during filling are 1.5 g/sec oil phase and 3.0 cc/sec water phase.

Once filled, agitation is begun, with the impeller turning at 1800 RPM. The aqueous phase is then evenly ramped up in flow to a rate of 43.50 cc/sec over a time period of 40 sec. The back pressure created by the dynamic and static mixers at this point is 8.5 PSI. The impeller speed is then ramped downwardly evenly to a speed of 1400 RPM over a period of 60 sec. The back pressure drops to 4.5 PSI. At this point the impeller speed is instantly increased to 1800 RPM. The system back pressure remains constant thereafter at 4.5 PSI.

The formed emulsion is collected in Rubbermaid Economy Cold Food Storage Boxes, constructed of food grade polyethylene, Model 3500, nominally 18 in. by 26 in. by 9 in. deep, having true inside dimensions of 15 in. by 23 in. by 9 in. deep. The molds are pretreated with a film of a solution comprising a 20% solution of SPAN ® 20 in xylene (which is also allowed to settle overnight, and only the clear supernatant is used). The molds are preheated, causing xylene to evaporate to leave only the SPAN® 20. Forty-seven liters of emulsion are collected in each mold.

The filled molds are then kept in a room maintained at 65° C. for 18 hours to cure the emulsion therein. After curing is complete, the wet cured foam material is removed from the curing boxes. The foam at this point contains about 30–40 times the weight of polymerized material (30–40×) of the residual water phase containing dissolved emulsifiers, electrolyte and initiator. The foam material is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6×) the weight of the polymerized material. At this point, the sheets are then resaturated with a 1% CaCl$_2$ solution at 60° C., are squeezed in a nip to a water phase content of about 10×.

The foam sheets, which now contain about 10× of what is essentially a 1% CaCl$_2$ solution are passed through a final nip equipped with a vacuum slot. The last nip reduces the CaCl$_2$ solution content to about 5 times (5×) the weight of polyer. The foam remains compressed after the final nip at a caliper of about 0.080 in. (0.2 cm). The foam is then dried in an air circulationg oven set at about 60° C. for about three hours. Such drying reduces the moisture content to about 5–7% by weight of polymerized material.

Such a foam is of the "thin-until-wet" type meaning that this foam will remain in a collapsed, relatively thin state upon dewatering but will reexpand in caliper when it encounters and subsequently imbibes aqueous body fluids. The thin-until-wet foam material prepared according to this Example IV will, in its expanded state, have an average cell size of about 12 microns.

HIPE emulsions, which are prepared in accordance with the continuous process herein and which are especially useful for subsequent polymerization and dewatering to form thin-until-wet absorbent foams, can be realized by selecting certain preferred processing parameters. In particular, thin-until-wet foam-forming HIPE emulsions can be prepared using:

A) Oil phase emulsifiers selected from sorbitan monolaurate (e.g., SPAN® 20) and combinations (e.g. in a 1:1 to 10:1 weight ratio) of sorbitan monolaurate (e.g., SPAN® 20) and a co-emulsifier selected from polyglycerol fatty acid esters and sorbitan monopalmitate (e.g., SPAN® 40).

B) A dynamic mixing zone temperature ranging from about 25° C. to 50° C. or even 25° C. to 60° C.;

C) Shear agitation in the dynamic mixing zone which is sufficient to eventually form a high internal phase emulsion that, upon subsequent polymerization, provides a foam having an average cell size of from about 5 to 30 microns; and preferably D) Relatively higher ratios of glassy monomer to rubbery comonomer in the oil phase such that, for example, the molar ratio of glassy monomer to rubbery comonomer ranges from about 1:2 to 1:1.

What is claimed is:

1. A continuous process for the preparation of a collapsed, but expandable, absorbent foam material made from a polymerized high internal phase emulsion, which process comprises:

A) providing a liquid feed stream of an oil phase comprising i) from about 3% to 41% by weight of a substantially water-insoluble, monofunctional glassy monomer component;

ii) from about 27% to 73% by weight of a substantially water-insoluble, monofunctional rubbery comonomer component;

iii) from about 8% to 30% by weight of a substantially water-insoluble, polyfunctional cross-linking agent component; and iv) from about 2% to 33% by weight of an emulsifier component selected from sorbitan monolaurate and combinations of sorbitan monolaurate with a co-emulsifier selected from polyglycerol fatty acid esters or sorbitan monopalmitate;

B) providing a liquid feed stream of a water phase comprising an aqueous solution containing from about 0.2% to 40% by weight of water-soluble electrolyte;

C) simultaneously introducing said liquid feed streams into a dynamic mixing zone at flow rates such the the initial weight ratio of water phase to oil phase being introduced ranges from about 2:1 to 10:1;

D) subjecting the combined feed streams in said dynamic mixing zone to sufficient shear agitation to at least partially form an emulsified mixture in said zone while maintaining steady, non-pulsating flow rates for the oil and water phase streams;

E) steadily increasing the ratio of water to oil feed streams being introduced into said dynamic mixing zone to within the range of from about 12:1 to 100:1 at a rate of increase which does not destroy the emulsified nature of the contents of said dynamic mixing zone, while maintaining the emulsified contents of said dynamic mixing zone at a temperature of from 25° C. to 60° C., and while subjecting the emulsified contents of said zone to continued shear agitation which is sufficient to eventually form a high internal phase emulsion that, upon subsequent polymerization, provides a foam having an average cell size of from about 5 to 30 microns;

F) continuously withdrawing the emulsified contents of said dynamic mixing zone and continuously introducing said emulsified contents into a static mixing zone wherein said emulsfied contents are further subjected to sufficient shear mixing to thereby completely form a stable high internal phase emulsion having a water to oil phase weight ratio of from about 12:1 to 100:1;

G) continuously withdrawing said stable high internal phase emulsion from said static mixing zone;

H) subjecting said stable high internal phase emulsion withdrawn from said static mixing zone to conditions suitable for effecting polymerization of the polymerizable monomers, comonomers and cross-linking agents in the oil phase of said stable high internal phase emulsion to thereby form a polymeric foam material; and I) dewatering said polymeric foam material to an extent which is sufficient to cause said foam material to collapse into an absorbent foam material which will reexpand upon contact with aqueous body fluids.

2. A process according to claim 1 wherein:

A) the emulsifier component of the oil phase consists essentially of sorbitan monolaurate; and B) the emulsified contents of the dynamic mixing zone are maintained at a temperature of from about 25° C. to 50° C.

3. A process according to claim 1 wherein:

A) the molar ratio of glassy monomer to rubbery comonomer in the oil phase ranges for about 1:2 to 1:1; and B) the emulsifier component of the oil phase comprises a combination of sorbitan monolaurate and a co-emulsifier in a monolaurate to co-emulsifier weight ratio ranging from about 1:1 to 10:1.

* * * * *